(12) United States Patent
Rains et al.

(10) Patent No.: US 8,739,801 B2
(45) Date of Patent: Jun. 3, 2014

(54) SYSTEM AND METHOD FOR IDENTIFYING A LANDMARK

(75) Inventors: James K. Rains, Cordova, TN (US); Nicholas S. Ritchey, Collierville, TN (US); Gene Edward Austin, Bartlett, TN (US); Henry B. Faber, Memphis, TN (US); Nathaniel Kelley Grusin, Germantown, TN (US); Tobias Schwägli, Solothurn (CH); William M. Ricci, Richmond Heights, MO (US)

(73) Assignee: Smith & Nephew, Inc., Memphis, TN (US)

( * ) Notice: Subject to any disclaimer, the term of this patent is extended or adjusted under 35 U.S.C. 154(b) by 1314 days.

(21) Appl. No.: 12/527,997

(22) PCT Filed: Feb. 28, 2008

(86) PCT No.: PCT/US2008/055300
§ 371 (c)(1),
(2), (4) Date: Feb. 12, 2010

(87) PCT Pub. No.: WO2008/106593
PCT Pub. Date: Sep. 4, 2008

(65) Prior Publication Data
US 2010/0152566 A1    Jun. 17, 2010

Related U.S. Application Data

(60) Provisional application No. 60/892,116, filed on Feb. 28, 2007, provisional application No. 60/911,907, filed on Apr. 15, 2007.

(30) Foreign Application Priority Data

Feb. 28, 2007   (WO) ................... PCTUS2007063001

(51) Int. Cl.
   *A61B 19/00*   (2006.01)

(52) U.S. Cl.
   USPC ........................................................ 128/899

(58) Field of Classification Search
   USPC ............. 128/899; 600/409, 424, 434; 606/72, 606/97, 130; 623/16.11
   See application file for complete search history.

(56) References Cited

U.S. PATENT DOCUMENTS 3,219,969 A   11/1965   Snavely
4,353,110 A   10/1982   Ellis (Continued)

FOREIGN PATENT DOCUMENTS

CA   2571508 A1   1/2006
CN   2698283 Y    5/2005

(Continued)

OTHER PUBLICATIONS

Office Action for Chinese Application No. 200880006490.9, mailed Mar. 31, 2011, 13 pages.

(Continued)

*Primary Examiner* — Christine Matthews
(74) *Attorney, Agent, or Firm* — Fish & Richardson P.C.

(57) ABSTRACT

A system (10, 110) for identifying a landmark is disclosed. The system includes a field generator (16, 116) for generating a magnetic field, an orthopaedic implant (30, 130) located within the magnetic field, the implant having at least one landmark (31) and a first magnetic sensor (32) spaced apart from the landmark, a landmark identifier (18, 118) with a second magnetic sensor (20, 120) and a processor (12, 112) for comparing sensor data from the first and second sensor and using the set distance to calculate the position of the landmark identifier relative to the at least one landmark. The system allows for blind targeting of one or more landmarks.

33 Claims, 10 Drawing Sheets

(56) References Cited

U.S. PATENT DOCUMENTS

| | | | |
|---|---|---|---|
| 4,532,599 | A | 7/1985 | Smith |
| 4,621,628 | A * | 11/1986 | Brudermann .................. 606/97 |
| D297,047 | S | 8/1988 | Hon et al. |
| 4,794,930 | A | 1/1989 | Machida et al. |
| 4,803,976 | A | 2/1989 | Frigg et al. |
| 5,049,151 | A | 9/1991 | Durham et al. |
| 5,127,913 | A | 7/1992 | Thomas |
| 5,217,009 | A | 6/1993 | Kronberg |
| 5,281,224 | A | 1/1994 | Faccioli et al. |
| 5,361,766 | A | 11/1994 | Nichols et al. |
| 5,383,917 | A | 1/1995 | Desai et al. |
| 5,411,503 | A | 5/1995 | Hollstien et al. |
| 5,417,688 | A | 5/1995 | Elstrom et al. |
| 5,433,720 | A | 7/1995 | Faccioli et al. |
| 5,514,145 | A | 5/1996 | Durham et al. |
| 5,580,156 | A | 12/1996 | Suzuki et al. |
| 5,584,838 | A | 12/1996 | Rona et al. |
| 5,585,783 | A | 12/1996 | Hall |
| 5,957,836 | A | 9/1999 | Johnson |
| 5,957,934 | A | 9/1999 | Rapoport |
| 6,009,878 | A | 1/2000 | Weijand et al. |
| 6,036,696 | A | 3/2000 | Lambrecht et al. |
| 6,039,742 | A | 3/2000 | Krettek et al. |
| 6,081,741 | A | 6/2000 | Hollis |
| 6,157,853 | A | 12/2000 | Blume et al. |
| 6,162,228 | A | 12/2000 | Durham |
| 6,174,335 | B1 | 1/2001 | Varieur et al. |
| 6,212,419 | B1 | 4/2001 | Blume et al. |
| 6,233,490 | B1 | 5/2001 | Kasevich |
| 6,267,770 | B1 | 7/2001 | Truwit |
| 6,304,091 | B1 | 10/2001 | Shahoian et al. |
| 6,311,082 | B1 | 10/2001 | Creighton et al. |
| 6,474,341 | B1 | 11/2002 | Hunter et al. |
| 6,503,249 | B1 | 1/2003 | Krause |
| 6,575,973 | B1 | 6/2003 | Shekalim |
| 6,636,757 | B1 | 10/2003 | Jascob et al. |
| 6,675,491 | B2 | 1/2004 | Sasaki et al. |
| 6,694,168 | B2 | 2/2004 | Traxel et al. |
| 6,718,194 | B2 | 4/2004 | Kienzle |
| 6,747,253 | B1 | 6/2004 | Firth et al. |
| 6,807,446 | B2 | 10/2004 | Fenn et al. |
| 6,890,332 | B2 | 5/2005 | Truckai et al. |
| 7,001,346 | B2 | 2/2006 | White |
| 7,029,478 | B2 | 4/2006 | Hollstien et al. |
| 7,060,075 | B2 | 6/2006 | Govari et al. |
| D528,211 | S | 9/2006 | Solar et al. |
| 7,130,676 | B2 | 10/2006 | Barrick |
| 7,152,608 | B2 | 12/2006 | Hunter et al. |
| 7,217,276 | B2 | 5/2007 | Henderson et al. |
| 7,253,611 | B2 * | 8/2007 | Ma et al. ................. 324/207.2 |
| 7,294,133 | B2 | 11/2007 | Zink et al. |
| 7,295,184 | B2 | 11/2007 | Suprun et al. |
| 7,358,481 | B2 | 4/2008 | Yeoh et al. |
| 7,477,926 | B2 | 1/2009 | McCombs |
| 7,532,997 | B2 | 5/2009 | Li et al. |
| 7,542,791 | B2 | 6/2009 | Mire et al. |
| 7,549,960 | B2 | 6/2009 | Govari |
| 7,575,550 | B1 | 8/2009 | Govari |
| 7,686,818 | B2 | 3/2010 | Simon et al. |
| 7,702,379 | B2 | 4/2010 | Avinash et al. |
| 7,727,240 | B1 | 6/2010 | Benton |
| 7,729,742 | B2 | 6/2010 | Govari |
| 7,785,330 | B2 | 8/2010 | Sherman et al. |
| 7,835,785 | B2 | 11/2010 | Scully et al. |
| 7,840,254 | B2 | 11/2010 | Glossop |
| 7,918,853 | B2 | 4/2011 | Watanabe et al. |
| 7,925,068 | B2 | 4/2011 | Hoctor et al. |
| 8,066,706 | B2 | 11/2011 | Schlienger et al. |
| 8,197,494 | B2 | 6/2012 | Jaggi et al. |
| 8,211,108 | B2 | 7/2012 | Matityahu |
| 8,301,262 | B2 | 10/2012 | Mi et al. |
| 2002/0032445 | A1 | 3/2002 | Fujiwara |
| 2002/0052604 | A1 | 5/2002 | Simon et al. |
| 2002/0173792 | A1 | 11/2002 | Severns et al. |
| 2003/0105470 | A1 | 6/2003 | White |
| 2003/0120150 | A1 | 6/2003 | Govari |
| 2003/0135211 | A1 | 7/2003 | Cho |
| 2003/0164172 | A1 | 9/2003 | Chumas et al. |
| 2003/0208122 | A1 | 11/2003 | Melkent et al. |
| 2004/0011365 | A1 | 1/2004 | Govari et al. |
| 2004/0034355 | A1 * | 2/2004 | Govari et al. .................. 606/72 |
| 2004/0243148 | A1 * | 12/2004 | Wasielewski ................ 606/130 |
| 2005/0027301 | A1 | 2/2005 | Stihl |
| 2005/0027304 | A1 | 2/2005 | Leloup et al. |
| 2005/0035115 | A1 | 2/2005 | Anderson et al. |
| 2005/0035116 | A1 | 2/2005 | Brown et al. |
| 2005/0043726 | A1 | 2/2005 | McHale et al. |
| 2005/0059885 | A1 | 3/2005 | Melkent et al. |
| 2005/0070916 | A1 | 3/2005 | Hollstien et al. |
| 2005/0075562 | A1 | 4/2005 | Szakelyhidi et al. |
| 2005/0075632 | A1 | 4/2005 | Russell et al. |
| 2005/0080335 | A1 | 4/2005 | Simon et al. |
| 2005/0080427 | A1 | 4/2005 | Govari et al. |
| 2005/0085714 | A1 | 4/2005 | Foley et al. |
| 2005/0085715 | A1 | 4/2005 | Dukesherer et al. |
| 2005/0099290 | A1 | 5/2005 | Govari |
| 2005/0124988 | A1 | 6/2005 | Terrill et al. |
| 2005/0143726 | A1 | 6/2005 | Bortkiewicz |
| 2005/0197569 | A1 | 9/2005 | McCombs |
| 2005/0228270 | A1 | 10/2005 | Lloyd et al. |
| 2005/0242087 | A1 | 11/2005 | Anderson et al. |
| 2005/0245821 | A1 | 11/2005 | Govari et al. |
| 2005/0261700 | A1 | 11/2005 | Tuma et al. |
| 2006/0015031 | A1 | 1/2006 | Kienzle |
| 2006/0029186 | A1 | 2/2006 | De et al. |
| 2006/0074405 | A1 | 4/2006 | Malackowski et al. |
| 2006/0084867 | A1 * | 4/2006 | Tremblay et al. ............. 600/434 |
| 2006/0142656 | A1 | 6/2006 | Malackowski et al. |
| 2006/0293593 | A1 | 12/2006 | Govari et al. |
| 2007/0093709 | A1 | 4/2007 | Abernathie |
| 2007/0129629 | A1 | 6/2007 | Beauregard et al. |
| 2007/0161888 | A1 * | 7/2007 | Sherman et al. ............... 600/409 |
| 2007/0162018 | A1 | 7/2007 | Jensen et al. |
| 2007/0167744 | A1 | 7/2007 | Beauregard et al. |
| 2007/0191827 | A1 | 8/2007 | Lischinsky et al. |
| 2007/0208251 | A1 | 9/2007 | Anderson et al. |
| 2007/0225595 | A1 | 9/2007 | Malackowski et al. |
| 2007/0255132 | A1 | 11/2007 | Shalgi et al. |
| 2007/0276370 | A1 | 11/2007 | Altarac et al. |
| 2007/0282440 | A1 | 12/2007 | Visentin |
| 2008/0039857 | A1 | 2/2008 | Giersch et al. |
| 2008/0086145 | A1 | 4/2008 | Sherman et al. |
| 2008/0221628 | A1 | 9/2008 | Milbocker et al. |
| 2008/0228195 | A1 | 9/2008 | von Jako et al. |
| 2008/0255560 | A1 | 10/2008 | Myers et al. |
| 2008/0269596 | A1 | 10/2008 | Revie et al. |
| 2008/0281326 | A1 | 11/2008 | Watanabe et al. |
| 2008/0281334 | A1 | 11/2008 | Zheng et al. |
| 2009/0024023 | A1 | 1/2009 | Welches et al. |
| 2009/0054910 | A1 | 2/2009 | Zheng et al. |
| 2009/0088756 | A1 | 4/2009 | Anderson |
| 2009/0099404 | A1 | 4/2009 | Kraus et al. |
| 2009/0165573 | A1 | 7/2009 | Ledoux et al. |
| 2009/0177080 | A1 | 7/2009 | Kristan et al. |
| 2009/0227862 | A1 | 9/2009 | Smith et al. |
| 2009/0306665 | A1 | 12/2009 | Lerner et al. |
| 2009/0306666 | A1 | 12/2009 | Czartoski et al. |
| 2009/0326537 | A1 | 12/2009 | Anderson |
| 2010/0041985 | A1 | 2/2010 | Simon et al. |
| 2010/0145337 | A1 | 6/2010 | Janna et al. |
| 2010/0152566 | A1 | 6/2010 | Rains et al. |
| 2010/0152573 | A1 * | 6/2010 | Ritchey et al. ................ 600/424 |
| 2010/0211177 | A1 | 8/2010 | Abdou |
| 2010/0274121 | A1 | 10/2010 | Ritchey et al. |
| 2010/0274256 | A1 | 10/2010 | Ritchey et al. |
| 2010/0274306 | A1 | 10/2010 | Pastore et al. |
| 2010/0289491 | A1 | 11/2010 | Budker et al. |
| 2010/0312245 | A1 | 12/2010 | Tipirneni et al. |
| 2011/0082366 | A1 | 4/2011 | Scully et al. |
| 2011/0109311 | A1 | 5/2011 | Walsh |
| 2011/0270080 | A1 | 11/2011 | Crane |
| 2011/0295108 | A1 | 12/2011 | Cox et al. |
| 2011/0295253 | A1 | 12/2011 | Bonutti et al. |
| 2012/0010500 | A1 | 1/2012 | Couture et al. |

(56) References Cited

U.S. PATENT DOCUMENTS

| | | |
|---|---|---|
| 2012/0035468 A1 | 2/2012 | Ritchey et al. |
| 2012/0091122 A1 | 4/2012 | Ahmad et al. |
| 2012/0143047 A1 | 6/2012 | Kimura et al. |
| 2012/0184844 A1 | 7/2012 | Gielen et al. |
| 2012/0220107 A1 | 8/2012 | Fukuda et al. |
| 2012/0227542 A1 | 9/2012 | Koch |

FOREIGN PATENT DOCUMENTS

| | | |
|---|---|---|
| DE | 102008023760 | 12/2009 |
| EP | 523905 | 5/1993 |
| EP | 628287 | 4/1995 |
| EP | 1391181 | 2/2004 |
| EP | 1570782 A2 | 9/2005 |
| EP | 1382308 A3 | 11/2005 |
| EP | 1570781 | 9/2009 |
| EP | 2130511 | 12/2009 |
| EP | 1743590 | 10/2010 |
| EP | 1803394 B1 | 1/2012 |
| GR | 1005791 | 1/2008 |
| WO | WO9500085 A1 | 1/1995 |
| WO | WO9713467 | 4/1997 |
| WO | WO9832387 A1 | 7/1998 |
| WO | WO9947052 | 9/1999 |
| WO | WO0134016 | 10/2001 |
| WO | WO03044556 A2 | 5/2003 |
| WO | WO03105659 | 12/2003 |
| WO | WO2004069063 | 8/2004 |
| WO | WO2005120203 A2 | 12/2005 |
| WO | WO2007025191 | 3/2007 |
| WO | WO2007009088 A3 | 5/2007 |
| WO | WO2007061890 | 5/2007 |
| WO | WO2007061890 A2 | 5/2007 |
| WO | WO2007133168 | 11/2007 |
| WO | WO2008105874 | 9/2008 |
| WO | WO2009108214 | 9/2009 |
| WO | WO2009131999 | 10/2009 |
| WO | WO2010028046 | 3/2010 |
| WO | WO2010099247 A2 | 9/2010 |
| WO | WO2010129141 | 11/2010 |
| WO | WO2010129308 A2 | 11/2010 |

OTHER PUBLICATIONS

International Search Report for International Application No. PCT/US2008/055300, mailed Sep. 17, 2008, 3 pages.
International Preliminary Report on Patentability and Written Opinion for International Application No. PCT/US2008/055300, mailed Sep. 1, 2009, 6 pages.
International Preliminary Report on Patentability and Written Opinion for International Application No. PCT/US2007/063001, mailed Sep. 1, 2009, 5 pages.
International Search Report for International Application No. PCT/US2007/063001, mailed Nov. 30, 2007, 3 pages.
Rains, et al., U.S. Appl. No. 12/919,255, filed Aug. 25, 2010.
International Search Report for International Application No. PCT/US2008/074520, mailed Jan. 23, 2009, 2 pages.
EKLIPTIK, "Guiding Star", reprinted from http://ekliptik.si/content/view/37/42, on Jul. 1, 2010, 2 pages.
Ritchey, et al., U.S. Appl. No. 29/376,026, filed on Sep. 30, 2010.
International Search Report and Written Opinion for International Application No. PCT/US2010/032634, mailed Jan. 26, 2011, 10 pages.
International Search Report and Written Opinion for PCT/US2010/030784, mailed Oct. 29, 2010, 11 pages.
Office Action for U.S. Appl. No. 12/547,716, mailed Apr. 2, 2012, 11 pages.
Office Action for U.S. Appl. No. 12/528,253, mailed Mar. 21, 2012, 9 pages.
Office Action for U.S. Appl. No. 12/758,747, mailed Apr. 10, 2012, 11 pages.
Ex Parte Quayle Action in U.S. Appl. No. 29/376,026, mailed Apr. 30, 2012, 10 pages.
Office Action for European Application 08872996.7-1269, Jul. 21, 2011, 5 pages.
"Innomed Hip Instruments—hohmann retractors," reprinted from http://www.innomed.net/hip_rets_hohmanns.htm on Jan. 6, 2011, 8 pages.
European Office Communication issued in Eurpoean Application No. 08 730 964.7-1269 dated Jun. 18, 2010.
International Search Report and Written Opinion for International Application No. PCT/US2010/051678, mailed Apr. 14, 2011, 8 pages.
Office Action for U.S. Appl. No. 12/919,255, mailed May 25, 2012.
First Office Action for Chinese Application No. 200880128908.3 mailed Apr. 24, 2012.
Association of Surgical Technologists, "AST Recommended Standards of Practice for Surgical Drapes," effective Apr. 13, 2008.
Ashar, Tom, "Ultrasound Guidance for Placement of Central Venous Catheters," Israeli Journal of Emergency Medicine, vol. 7, No. 2, Jun. 2007.
Buckner, C., et al., "Real-Time Sonography wth Electromagnetic Tracking Navigation for Biopsy of a Hepatic Neoplasm Seen on on Arterial Phase Computed Tomography," J Ultrasound Med 2011, 30:253-256.
"GE Heathcare: Ultrasound Imaging Accessories, vol. 6," CIVco Medical Solutions, Multi-Modality Imaging, 2011.
"Guiding Star with the LIDIS module," Ekliptik, 2007.
Ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
Ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonavsolutions.pdf.
GE Healthcare, "Interventional X-ray, OEC C-arm," 2012.
Office Action for U.S. Appl. No. 13/123,792, mailed Sep. 14, 2012.
Office Action for U.S. Appl. No. 13/323,010, mailed Aug. 14, 2012.
Office Action for U.S. Appl. No. 12/528,253, mailed Aug. 16, 2012.
International Search Report and Written Opinion for International Application PCT/US2012/022481, mailed Jul. 31, 2012.
Office Action for U.S. Appl. No. 12/547,716, mailed Sep. 18, 2012.
Second Office Action for Chinese Application No. 200880006490.9 mailed Apr. 26, 2012.
Office Action for Australian Patent Application No. 2008221332, dated Jun. 15, 2012.
Office Action for U.S. Appl. No. 12/758,747, mailed Nov. 15, 2012.
Office Action for U.S. Appl. No. 12/919,255, mailed Jan. 8, 2013.
Office Action for U.S. Appl. No. 12/768,689, mailed Nov. 14, 2012.
Office Action for U.S. Appl. No. 12/768,689, mailed Jun. 5, 2012.
Notice of Reasons for Rejection for Japanese Application No. 2010-548660 mailed Jan. 15, 2013.
Office Action for U.S. Appl. No. 13/030,801, mailed Mar. 13, 2013.
Office Action for U.S. Appl. No. 13/323,010, mailed Jun. 4, 2013.

\* cited by examiner

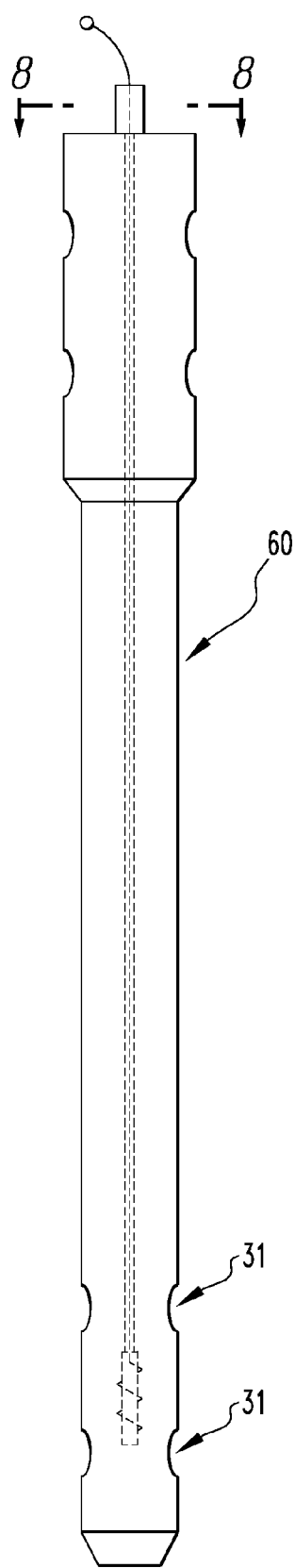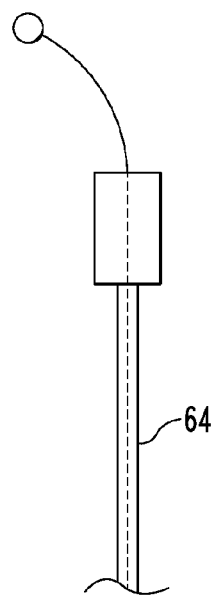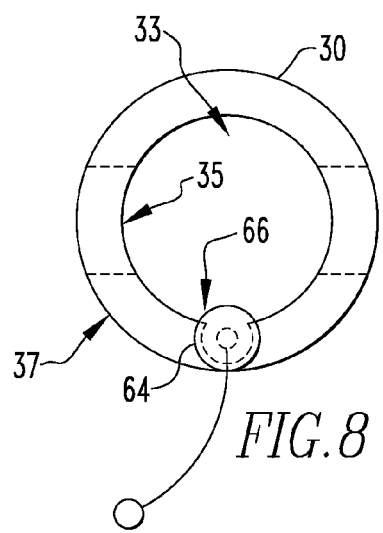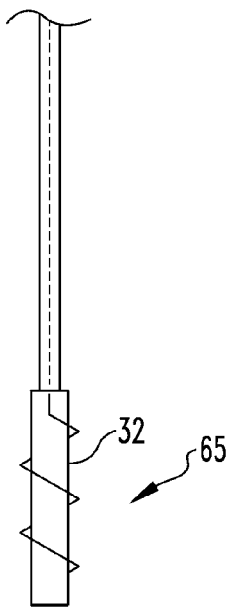
FIG. 6
FIG. 7
FIG. 8

SYSTEM AND METHOD FOR IDENTIFYING A LANDMARK

CROSS-REFERENCE TO RELATED APPLICATIONS

This application is a U.S. National Phase filing of International Application No. PCT/US2008/055300 and claims the benefit of U.S. Provisional Application No. 60/892,116, filed Feb. 28, 2007; and U.S. Provisional Application No. 60/911,907, filed Apr. 15, 2007. The disclosure of each prior application is incorporated herein by reference in its entirety.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

Embodiments of the present invention generally relate to orthopaedic implants and, more specifically, to identification of blind landmarks on orthopaedic implants.

2. Related Art

The interlocking femoral nail has significantly widened the scope for intramedullary (IM) fixation of long bone fractures. Locking an IM nail makes the construct more stable longitudinally and stops rotation of the nail within the bone. A typical IM nail fixation surgery involves a combination of jigs, x-ray imaging, and manual eye-balling to locate and drill the distal screw holes.

In this surgical procedure, an IM nail is hammered into the canal of a fractured long bone in order to fixate the fractured ends together. Typically, the proximal locking is performed first and is usually carried out with a jig. Nail deformation during intramedullary insertion, however, may make a jig inaccurate for the distal screws. The primary difficulty lies in the positioning of the distal locking screws and alignment of the drill for the drilling of the distal screw holes because it is the most time consuming and challenging step of the overall implantation procedure. Consequently, the two main reasons for failure in distal locking are incorrect entry point on the bone and wrong orientation of the drill. If either of these two factors is wrong, then the drill will not go through the nail hole.

An inaccurate entry point also compounds the problem as the rounded end of the drill bit often slips, and it is then difficult to place another drill hole next to the earlier one. Inaccurate distal locking may lead to premature failure with breakage of the nail through the nail hole, breakage of the screw, or the breaking of the drill bit within the bone.

Manual techniques are the most common and accepted techniques for sighting the distal screw holes and predominate the orthopaedic industry. The majority of distal targeting techniques employ a bushing (cylindrical sleeve) that guides the drill. The mechanism of aligning the guide bushing and keeping it in place differs. There are cases where the surgeons use a half sleeve (bushing cut in half longitudinally) to help steady the drill bit during drilling. In either situation, the surgeon will incise the patient and insert the drill through the incision. The manual techniques are based primarily on the surgeon's manual skill and make use of radiographic x-ray imaging and mechanical jigs.

Another method for achieving this on long nails is by using a technique called "perfect circles" with the aid of a C-arm. This is where one orients the patient and the C-arm such that when viewing the implant fluoroscopically the hole with which the screw is to pass appears to be in the shape of a circle. If the C-arm is not perpendicular to the hole then it would appear oblong or even absent.

There remains a need in the art for a system and method for targeting landmarks of a medical implant. Further, there remains a need in the art for accurately positioning the distal locking screws and aligning the drill for the drilling of the distal screw holes.

SUMMARY OF THE INVENTION

There is provided a system for identifying a landmark, the system comprising: a field generator for generating a magnetic field; an orthopaedic implant located within the magnetic field, the orthopaedic implant having at least one landmark and a longitudinal groove with a proximal end portion and a distal end portion; a first magnetic sensor mounted to the orthopaedic implant at the distal end portion of the longitudinal groove and spaced apart from the at least one landmark a set distance; a landmark identifier having a second magnetic sensor; and a processor for comparing sensor data from the first and second sensor and using the set distance to calculate the position of the landmark identifier relative to the at least one landmark.

According to some embodiments, the landmark is selected from the group consisting of a structure, a void, a boss, a channel, a detent, a flange, a groove, a member, a partition, a step, an aperture, a bore, a cavity, a dimple, a duct, a gap, a notch, an orifice, a passage, a slit, a hole, or a slot.

According to some embodiments, the orthopaedic implant is an intramedullary nail.

According to some embodiments, the orthopaedic implant has an outer surface, an inner surface forming a cannulation, and a wall therebetween, and the first magnetic sensor is mounted within the wall.

According to some embodiments, the orthopaedic implant further includes a pocket and the first sensor is located within the pocket.

According to some embodiments, the orthopaedic implant further includes a cover.

According to some embodiments, the orthopaedic implant further includes a second opening adapted to receive a cover.

According to some embodiments, the orthopaedic implant further includes a circumferential pocket.

According to some embodiments, the system includes a lead connected to the first magnetic sensor.

According to some embodiments, the system includes an insertion handle removably attached to the orthopaedic implant.

According to some embodiments, the system includes a monitor electrically connected to the processor.

According to some embodiments, the system includes a removable lead connected to the first sensor.

According to some embodiments, the longitudinal groove is along an outer surface of the implant.

According to some embodiments, the orthopaedic implant further includes a cannulation, and the longitudinal groove is generally adjacent the cannulation.

According to some embodiments, the landmark identifier includes a drill sleeve.

According to some embodiments, the landmark identifier further includes a serrated tip.

According to some embodiments, the landmark identifier further includes a tube.

According to some embodiments, the landmark identifier further includes a marking sensor.

According to some embodiments, the landmark identifier further includes a handle.

According to some embodiments, the processor provides feedback information to a user.

There is provided a system for identifying a landmark, the system comprising: a field generator for generating a magnetic field; an orthopaedic implant located within the magnetic field, the orthopaedic implant having at least one landmark; a magnet mounted to the orthopaedic implant and spaced apart from the at least one landmark a set distance; a landmark identifier having a magnetic sensor; and a processor for comparing sensor data from the magnetic sensor and using the set distance to calculate the position of the landmark identifier relative to the at least one landmark.

There is provided a method for identifying a landmark, the method comprising: providing an orthopaedic implant assembly having an orthopaedic implant with a longitudinal groove and a removable lead having a magnetic sensor attached thereto situated within the longitudinal groove, the orthopaedic implant having a proximal end portion, a distal end portion, and at least one landmark on the distal end portion; implanting the orthopaedic implant assembly in a patient; first installing transfixion elements in the proximal end portion; identifying the at least one landmark using a landmark identifier; installing a transfixion element in the at least one landmark in the distal end portion after first installing transfixion elements in the proximal end portion; and removing the removable lead.

There is provided a graphical user interface, comprising: a first portion indicating drill depth relative to an implant; and a second portion indicating landmark identifier position relative to a landmark located on the implant.

The invention has several advantages over prior devices and techniques. First, the invention operates independently of fluoroscopy and eliminates the necessity of X-ray devices for targeting of transfixion elements, thereby reducing the exposure of users and patients to radiation. Second, the invention allows a user to lock the driving-end before locking the non-driving end. In other words, the invention does not require use of an implant cannulation and allows for proximal locking prior to distal locking, in some embodiments.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings:

FIG. 6 illustrates an orthopaedic implant assembly in a second embodiment;

FIG. 7 is a front view of a removable lead;

FIG. 8 is a top view of the orthopaedic implant assembly shown in FIG. 6;

DETAILED DESCRIPTION OF THE EMBODIMENTS

Figure 1:
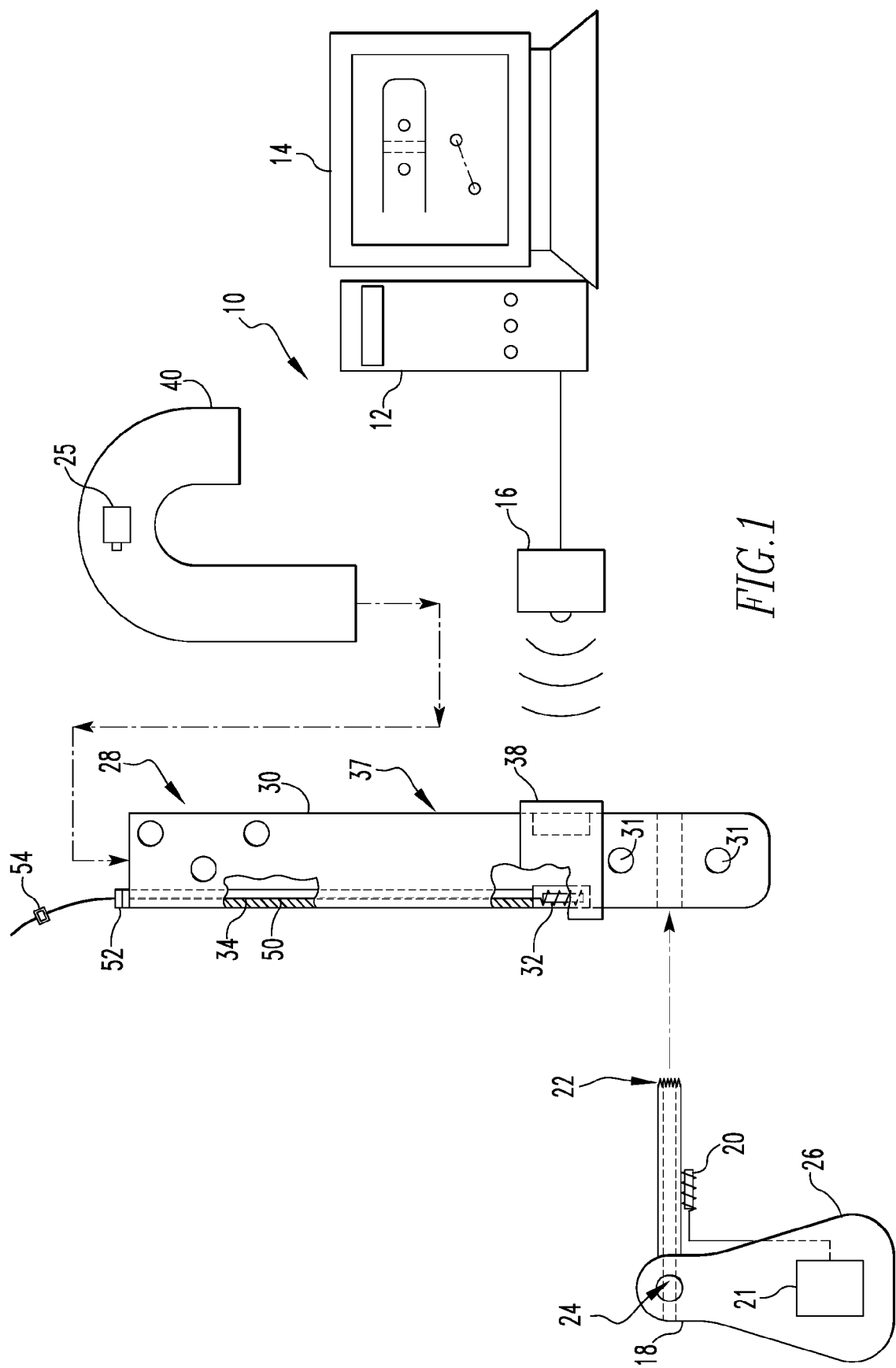
FIG. 1 illustrates a system for identifying a landmark in a first embodiment.

Referring to the accompanying drawings in which like reference numbers indicate like elements, FIG. 1 illustrates a system 10 for identifying a landmark in a first embodiment. The system 10 includes a processor 12, a magnetic field generator 16, a landmark identifier 18, and an orthopaedic implant assembly 28. In some embodiments, the system 10 further includes a monitor 14 electrically connected to the processor 12 and an insertion handle 40 removably attached to the orthopaedic implant assembly 28. The processor 12 is depicted as a desktop computer in FIG. 1 but other types of computing devices may equally be used. As examples, the processor 12 may be a desktop computer, a laptop computer, a personal data assistant (PDA), a mobile handheld device, or a dedicated device. In the depicted embodiment, the magnetic field generator is a device available from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other generators may be used. As examples, the field generator 16 may provide a pulsed direct current electromagnetic field or an alternating current electromagnetic field. In some embodiments, the system 10 further includes a control unit (not shown) connected to the magnetic field generator 16. The control unit controls the field generator, receives signals from small mobile inductive sensors, and communicates with the processor 12, either by wire or wirelessly. In some embodiments, the control unit may be incorporated into the processor 12 either through hardware or software.

The system 10 is a magnetic position tracking system. Magnetic tracking systems are well known and several variants have been developed. For illustrative purposes, the system 10 includes a magnetic field generator 16 comprised of suitably arranged electromagnetic inductive coils that serve as the spatial magnetic reference frame (i.e., X, Y, Z). The system 10 further includes small mobile inductive sensors, which are attached to the object being tracked. It should be understood that other variants could be easily accommodated. The position and angular orientation of the small mobile inductive sensors are determined from its magnetic coupling to the source field produced by magnetic field generator 16.

It is noted that the magnetic field generator 16 generates a sequence, or set, of here six, different spatial magnetic field shapes, or distributions, each of which is sensed by the small mobile inductive sensors. Each sequence enables a sequence of signals to be produced by the small mobile inductive sensors. Processing of the sequence of signals enables determination of position and/or orientation of the small mobile inductive sensors, and hence the position of the object to which the small mobile inductive sensor is mounted relative the magnetic coordinate reference frame which is in fixed relationship to the magnetic field generator 16. The processor 12 or the control unit uses the reference coordinate system and the sensed data to create a transformation matrix comprising position and orientation information.

The landmark identifier 18 is used to target a landmark, such as a landmark on the orthopaedic implant assembly 28. The landmark identifier 18 includes one or more small mobile inductive sensors. In the depicted embodiment, the landmark identifier 18 has a second sensor 20. The landmark identifier 18 may be any number of devices. As examples, the landmark identifier may be a drill guide, a drill sleeve, a drill, a drill nose, a drill barrel, a drill chuck, or a fixation element. In the embodiment depicted in FIG. 1, the landmark identifier 18 is a drill sleeve with a serrated tip 22, a tube 24, and a handle 26. The tube 24 also may be referred to as a bushing, cylinder, guide, or drilling/screw placement guide. In the depicted embodiment, the second sensor 20 is oriented relative to an axis of the tube 24, which may receive a drill. This offset of the sensor 20 from the tube 24 allows the position and orientation of the tube to be located in space in six dimensions (three translational and three angular) relative to the magnetic field generator 16 or another sensor in the system. In some embodiments, the processor 12 may need to be calibrated to adjust for the offset distance of the second sensor 20. In some embodiments, the landmark identifier 18 and the field generator 16 may be combined into a single component. For example, the field generator 16 may be incorporated within the handle 26.

The orthopaedic implant assembly 28 includes an implant 30 and one or more small mobile inductive sensors. In the depicted embodiment, the orthopaedic implant assembly 28 has a first sensor 32. In the embodiment depicted in FIG. 1, the implant 30 is in the form of intramedullary nail but other types of implants may be used. As examples, the implant may be an intramedullary nail, a bone plate, a hip prosthetic, or a knee prosthetic. The first sensor 32 is oriented and in a predetermined position relative to one or more landmarks on the implant 30. As examples, the landmark may be a structure, a void, a boss, a channel, a detent, a flange, a groove, a member, a partition, a step, an aperture, a bore, a cavity, a dimple, a duct, a gap, a notch, an orifice, a passage, a slit, a hole, or a slot. In the embodiment depicted in FIG. 1, the landmarks are transfixion holes 31. The offset of the first sensor 32 from the landmark allows the position of the landmark to be located in space in six dimensions (three translational and three angular) relative to the magnetic field generator 16 or another sensor in the system, such as the second sensor. In some embodiments, the processor may need to be calibrated to adjust for the offset distance of the first sensor 32.

The first sensor 32 and the second sensor 20 are connected to the processor 12. This may be accomplished by wire or wirelessly. The first sensor 32 and the second sensor 20 may be a six degree of freedom sensor configured to describe the location of each sensor in three translational axes, generally called X, Y and Z and three angular orientations, generally called pitch, yaw and roll. By locating the sensor in these reference frames, and knowing the location and orientation of each sensor, the landmark identifier 18 may be located relative to the landmark on the implant 30. In one particular embodiment, the information from the sensors allows for a surgeon to plan the surgical path for fixation and properly align a drill with a blind fixation hole. In the depicted embodiment, the sensors 32, 20 are six degrees of freedom sensor from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other sensors may be used.

The first sensor 32 may be attached to the implant 30. For example, the first sensor 32 may be attached to an outer surface 37. In the embodiment depicted in FIG. 1, the implant 30 further includes a groove 34 and a pocket 36. The groove 34 and pocket 36 are located in a wall of the implant 30. In the depicted embodiment, the first sensor 32 is intended to be attached to the implant 30 and installed in a patient for the service life of the implant 30. Further, in some embodiments, the orthopaedic implant assembly 28 includes a cover 38 to cover the pocket 36 and/or the groove 34. The cover 38 may be substantially flush with the external surface 37 of the implant 30. Accordingly, in some embodiments, the implant 30 includes a second opening 39 to receive the cover 38.

The first sensor 32 may be tethered to leads for communication and power. The leads, and the sensor, may be fixed to the implant 30. A lead 50 connects to the first sensor 32. A first connector 52 is used to place the lead 50 relative to the implant 30. A second connector 54 may be used to connect the lead 50 to another device, such as the processor 12 or the insertion handle 40.

The first sensor 32 may be fixed in the pocket 36 using a range of high stiffness adhesives or polymers including epoxy resins, polyurethanes, polymethyl methacrylate, polyetheretherketone, UV curable adhesives, silicone, and medical grade cyanoacrylates. As an example, EPO-TEK 301 available from Epoxy Technology, 14 Fortune Drive, Billerica, Mass. 01821 may be used. The lead 50 may be fixed in the groove in a similar manner. These types of fixation methods do not adversely affect the performance of the electrical components. Thereafter, the cover 38 may be placed on the implant 30 and welded in-place. For example, the covers may be laser welded to the implant.

The monitor 14 may be configured to display the position and orientation of the first sensor 32 and the second sensor 20 so that the display may show a surgeon both sensor positions and orientations relative to one another. The processor 12 may send positional data, either by wire or wirelessly, to a user interface, which may graphically display the relative positions of the landmark identifier and the implant on the monitor. The monitor 14 may be oriented relative to the landmark identifier so that the surgeon may visualize the user interface as an extension of the landmark identifier. The user interface also may be oriented so that the surgeon may view the monitor simultaneously with the surgical field.

The insertion handle 40 may be used for installation of the orthopaedic implant assembly 28 and also may be used to route the leads from the first sensor 32. For example, the insertion handle 40 may route both communication and power leads between the implant 30 and the processor 12.

In the embodiment depicted in FIG. 1, the landmark identifier 18 and the insertion handle 40 each include a communications module 21, 25 for wirelessly transmitting data from the sensor 20, 32 to the processor 12, but those skilled in the art would understand that other methods, such as by wire, may be used. In the depicted embodiment, the second connector 54 plugs into the communications module 25. Alternatively, and as is explained in greater detail below, the implant 30 and the insertion handle 40 may have mating electrical contacts that form a connection when the components are assembled such that the first sensor 32 is connected to the communications module 25.

In some embodiments, the implant 30 may include a communications circuit and an antenna for wireless communication. Power for the first sensor 32 and/or the communications circuit may be positioned within the insertion handle 40. For example, a battery may be placed within the insertion handle 40 for transferring power to the first sensor 32 and/or other electronics. Alternatively, the communications circuit, the antenna, and the battery may be located within the insertion handle 40 and each of these may be tethered to the first sensor 32. In yet another embodiment, the implant 30 may include a coil to inductively power the communications circuit and communicate data from the first sensor 32. The power source may be a single source mode or may be a dual mode AC/DC.

In use, the orthopaedic implant assembly 28 is installed in a patient. For example, in the case of internal fixation, the intramedullary nail is placed within an intramedullary canal. Optionally, the user may use transfixion elements, such as screws, to first lock the proximal end of the intramedullary nail. An operator uses the targeting device 18 and the first sensor 32 to identify the landmarks 31. For example, in the case of intramedullary nail fixation, a surgeon uses the targeting device 18 to identify the blind transfixion holes and drill through the holes for placement of a transfixion element.

Figure 2:
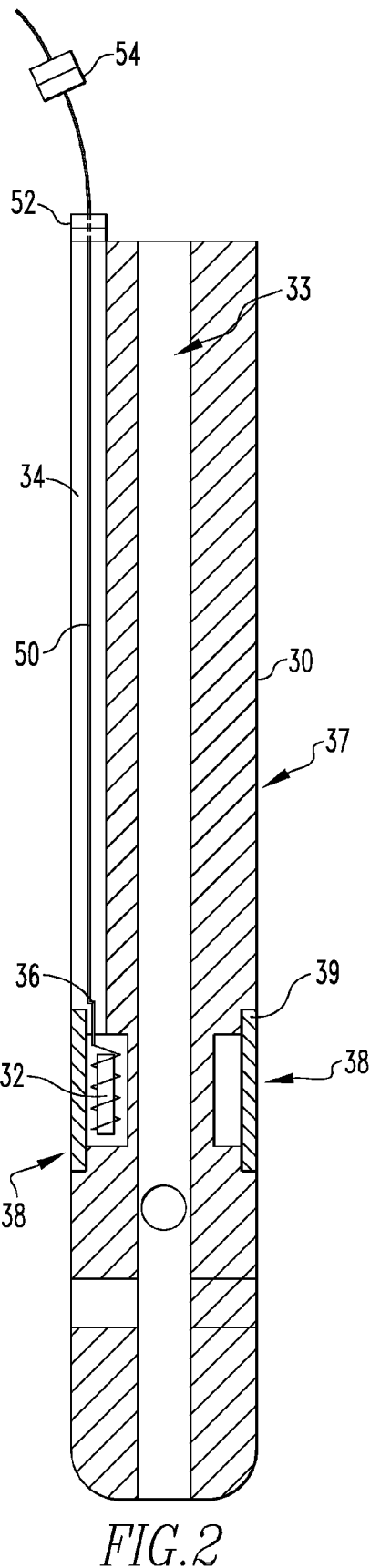
FIG. 2 is a sectional view of an orthopaedic implant assembly in a first embodiment.

FIG. 2 further illustrates the implant 30 as shown in FIG. 1. The implant 30 includes the first sensor 32, the longitudinal groove 34, the pocket 36, the cover 38, and the second opening 39. As examples, the cover 38 may be comprised of gold or titanium foil. In some embodiments, the implant 30 includes an inner surface 35 that forms a cannulation 33. The implant 30 includes the outer surface 37.

Figure 3:
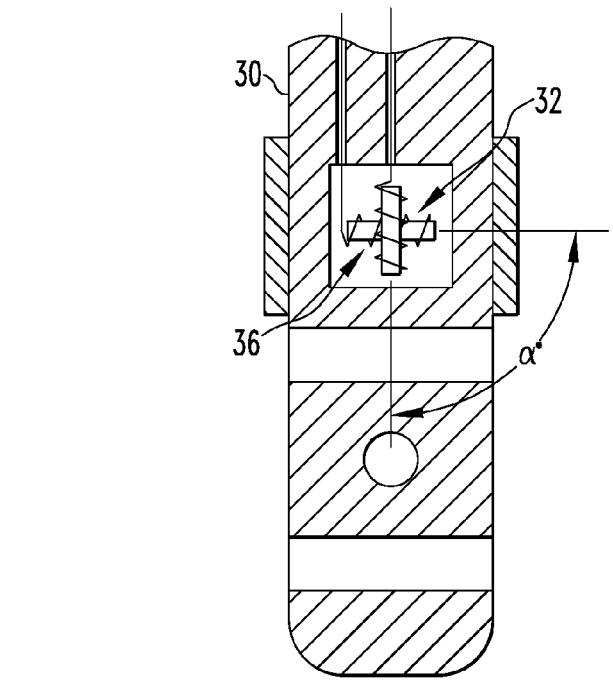
FIG. 3 illustrates a sensor mounting in a first embodiment.

FIG. 3 illustrates a first embodiment of the first sensor 32. The first sensor 32 includes two coils cross-layer to one another and having an angle alpha.

Figure 4:
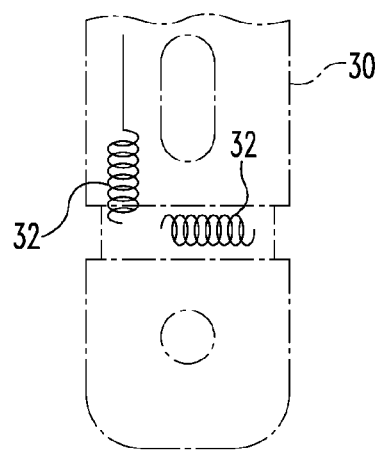
FIG. 4 illustrates sensor mounting in a second embodiment.
Figure 5:
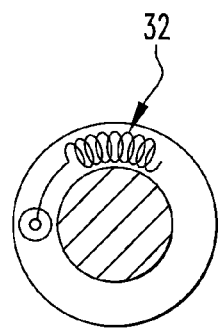
FIG. 5 illustrates the sensor shown in FIG. 4.

FIGS. 4 and 5 illustrate a second embodiment of the first sensor 32. The first sensor includes two coils generally orthogonal to one another in order to establish the orientation and position in the six degrees of freedom. A first coil may be oriented along the length of the implant 30. The second coil may be oriented either wrapped around the circumference of the implant, for example in a groove, or along the radius of the implant 30. In addition, while it is preferred to have the coils perpendicular to one another, other orientations may be used, although the mathematics may be more complex. Further, the coils may be oriented spirally around the implant 30. Such an orientation may allow two coils to be placed perpendicular to each other with both coils placed along both the length of the implant and along the circumference of the implant 30.

FIGS. 6-8 illustrate a second embodiment of the orthopaedic implant assembly 60. The orthopaedic implant assembly 60 includes the implant 30. In the embodiment depicted in FIG. 6, the implant 30 includes landmarks in the form of transfixion holes 31. The implant 30 includes a longitudinal internal groove 66 and a removable lead 64. In the embodiment depicted in FIG. 8, a diameter of the longitudinal groove 66 is shown as intersecting with the cannulation 33; however, in other embodiments, the diameter of the longitudinal internal groove is contained between the outer surface 37 and the inner surface 35. The removable lead 64 includes the first sensor 32 at its distal end portion 65. The first sensor 32 is located a known offset from the landmarks 31. The implant in FIGS. 6-8 is comprised of biocompatible material, and may be a metal alloy or a polymer. The longitudinal groove 66 may be machined or molded in place.

In use, the implant 30 with the removable lead is installed in a patient. For example, in the case of internal fixation, the intramedullary nail is placed within an intramedullary canal. Optionally, the user may use transfixion elements, such as screws, to first lock the proximal end of the intramedullary nail. An operator uses the targeting device 18 and the first sensor 32 to identify the landmarks 31. For example, in the case of intramedullary nail fixation, a surgeon uses the targeting device 18 to identify the blind transfixion holes and drill through the holes for placement of a transfixion element. After the implant 30 is secured, the operator removes the removable lead 64 and it is discarded.

Figure 9:
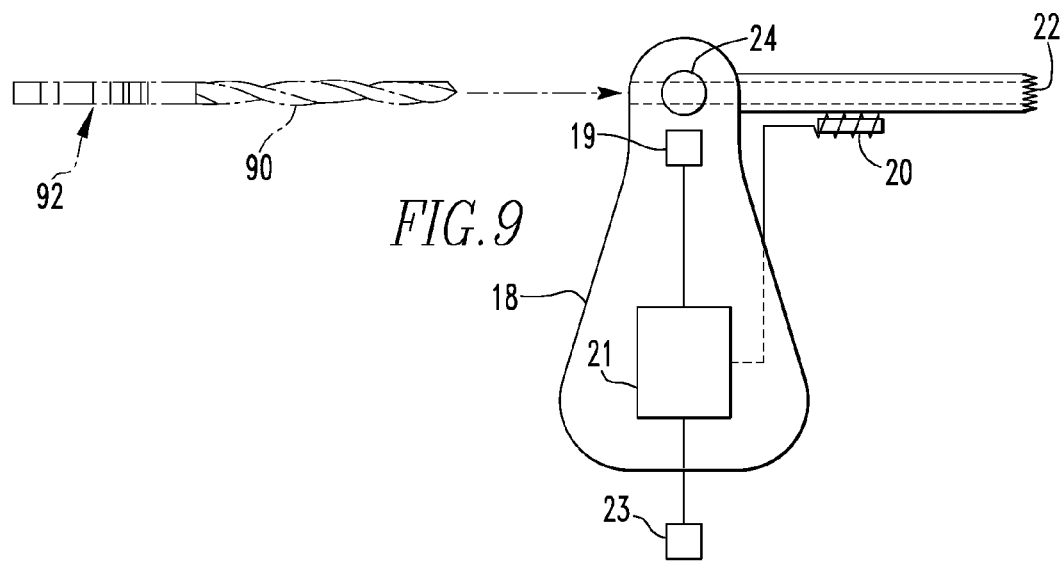
FIG. 9 illustrates a landmark identifier.

FIG. 9 further illustrates the landmark identifier 18 as shown in FIG. 1. The landmark identifier 18 includes the sensor 20, the serrated tip 22, the tube 24, and the handle 26. A drill 90 has markings 92 that interact with a marking sensor 19 adjacent the tube 24. The interaction is similar to a pair of digital measuring calipers in that the position between marking 92 and sensor 19 equate to a distance. This distance can be used to determine the depth of the drill into the bone and ultimately the length of the bone screw that will be inserted into the drilled hole. Distance, or drill depth, readings are only obtainable when the sensors 92 and 19 are in close proximity to each other, i.e. the drill 90 is inside the tube 24. Exemplary measurement devices are shown in U.S. Pat. No. 6,675,491 issued on Jan. 13, 2004 to Sasaki et al. and in U.S. Pat. No. 7,253,611 issued on Aug. 7, 2007 to Me et al., each of which is incorporated by reference. In the depicted embodiment, the marking sensor 19 is connected to the communications module 21. Alternatively, the marking sensor 19 may be connected by wire to the processor 12. In FIG. 9, the communications module 21 includes a third connector 23 for electrical connection to the processor 12.

Figure 10:
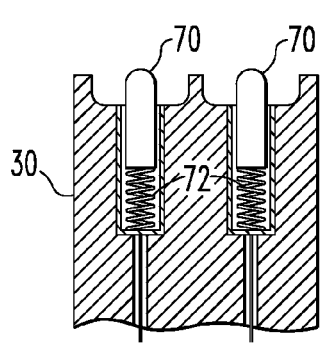
FIG. 10 is a sectional view illustrating point contacts in a first embodiment.
Figure 11:
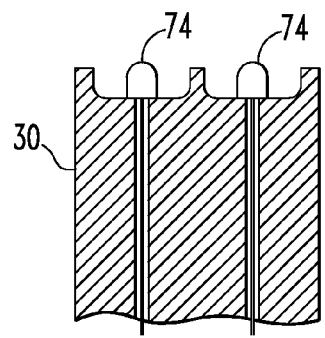
FIG. 11 is a sectional view illustrating point contacts in a second embodiment.
Figure 12:
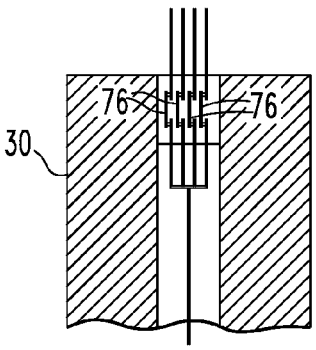
FIG. 12 is a sectional view illustrating a crimp electrical connection.

FIGS. 10-12 illustrate exemplary methods of electrically connecting the implant 30 to the insertion handle 40, which has corresponding electrical contacts. In FIG. 10, biasing elements 72 bias contacts 70 toward the insertion handle 40. In FIG. 11, the implant 30 has elastomeric electrical contacts 74. In FIG. 12, wires extending between the lead 50 and another component are crimped together at junction 76. In one method, the wires are torn free and separated at the junction 76 after installation of the orthopaedic implant assembly 28. In yet another method, the wires are cut above the junction 76 after installation of the orthopaedic implant assembly 28.

Figure 13:
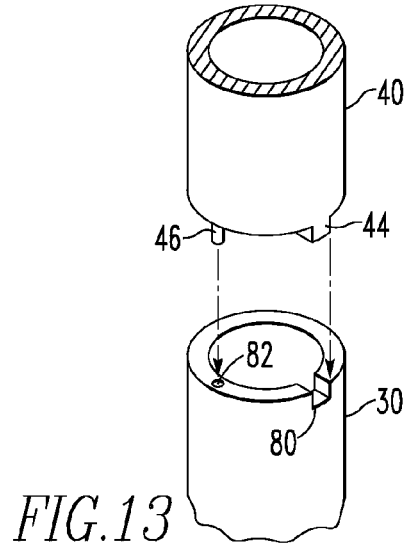
FIG. 13 is a partial perspective view illustrating alternative mechanisms for aligning the orthopaedic implant and the insertion handle.

Referring now to FIG. 13, the implant 30 and/or the insertion handle 40 may includes one or more alignment features 44 and mating notch 80 or alignment pin 46 and mating hole 82. The insertion handle may be configured to align with an upper surface of the implant. In one embodiment, the insertion handle may have a key configured to mate to a slot on the fixation member. Other alignment guides may be used. In addition, the guide may have an electrical connector configured to mate to an electrical connector on the fixation member. The connection between the guide and the fixation member may be spring loaded to ensure electrical contact between the electrical connectors. In order to avoid shorting the connection between the guide and the fixation member, the electrical connector may be insulated. As another example of electrically connecting the insertion handle to the implant, the electrical connectors may include a post and slip rings. The rings may be located on the implant, and the posts located on the insertion handle. The posts are biased to contact the rings. In such an embodiment, the angular location of the insertion handle relative to the axis of the implant is not fixed. This would allow the insertion handle to be positioned to the implant irrespective of angular position.

Figure 14:
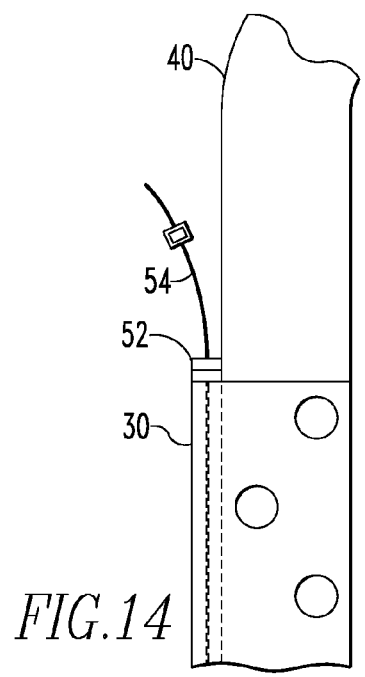
FIG. 14 illustrates connection of the insertion handle to the orthopaedic implant.

Referring now to FIG. 14, the implant 30 and the insertion handle 40 may be sized such that space remains available for the first connector 52 even when the components are assembled or mated.

As an example, the system for identifying a landmark may be used to target blind screw holes of an implanted intramedullary nail. The intramedullary nail is implanted in the patient. The electromagnetic field generator is activated. The processor receives signals from the sensor mounted to the intramedullary nail and from the sensor mounted to the landmark identifier, such as a drill sleeve. A computer program running on the processor uses the information of the at least two sensors and graphically display them in relative position on the monitor. A surgeon moves the landmark identifiers into position using feedback provided by the processor. When the landmark identifier is in the proper location, the surgeon drill through bone and the intramedullary nail to create a screw hole. In some embodiments, the processor may provide feedback as to the depth of the drilled hole. The surgeon may then place a screw through the drilled hole to affix the blind hole of the intramedullary nail.

Figure 15:
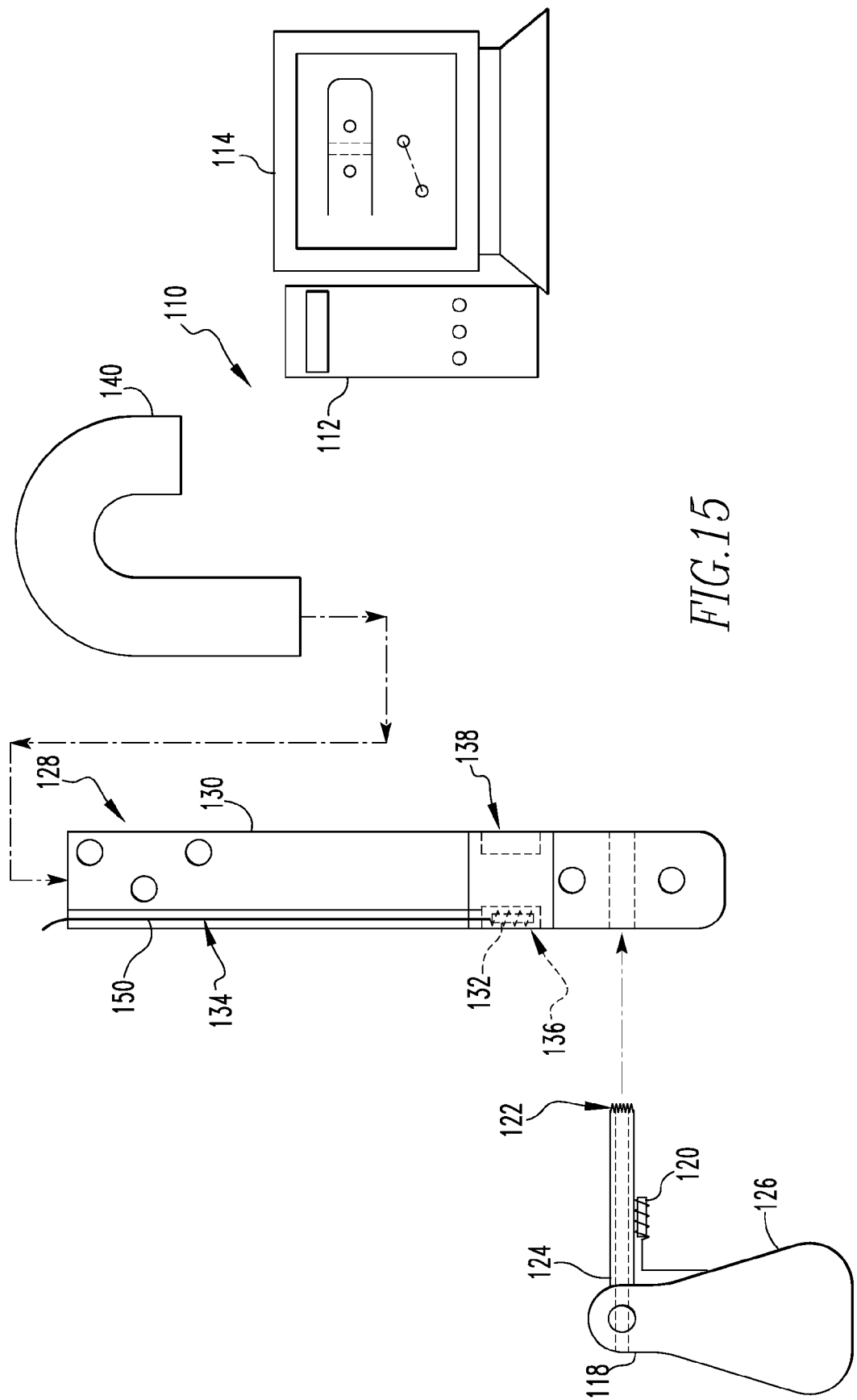
FIG. 15 illustrates the system for identifying a landmark in a second embodiment.

FIG. 15 illustrates a system 110 for identifying a landmark in a second embodiment. The system 110 includes a processor 112, a landmark identifier 118, and an orthopaedic implant assembly 128. In some embodiments, the system 110 further includes a monitor 114 and an insertion handle 140.

The landmark identifier 118 is used to target a landmark. The landmark identifier 118 includes a second sensor 120. In the embodiment depicted in FIG. 15, the landmark identifier 118 is a drill sleeve with a serrated tip 122, a tube 124, and a handle 126. In the depicted embodiment, the second sensor 120 is oriented relative to an axis of the tube, which may receive a drill. This offset of the sensor from the tube allows the position of the tube to be located in space in six dimensions (three translational and three angular) relative to the transmitter or another sensor in the system. In some embodiments, the processor may need to be calibrated to adjust for the offset distance of the second sensor 120.

The orthopaedic implant assembly 128 includes an implant 130 and a magnet 132. The magnet may be a permanent magnet or an electromagnet. The magnet 132 is oriented in a predetermined position relative to a landmark on the orthopaedic implant 130. This offset of the magnet from the landmark allows the position of the landmark to be located in space in six dimensions (three translational and three angular) relative to the transmitter or another sensor in the system, such as the second sensor. In some embodiments, the processor may need to be calibrated to adjust for the offset distance of the magnet 132. In the embodiment depicted in FIG. 1, the implant 130 further includes a pocket 136 and a cover 138. In the case of an electromagnet, a lead 150 connects to the magnet 132 and is contained within a groove 134.

As an example, the system for identifying a landmark may be used to target blind screw holes of an implanted intramedullary nail. The intramedullary nail is implanted in the patient. The processor receives signals from the sensor mounted to the landmark identifier, such as a drill sleeve. A computer program running on the processor uses the information of the sensor and graphically displays the sensor in relative position to the magnet on the monitor. A surgeon moves the landmark identifiers into position using feedback provided by the processor. When the landmark identifier is in the proper location, the surgeon drill through bone and the intramedullary nail to create a screw hole. In some embodiments, the processor may provide feedback as to the depth of the drilled hole. The surgeon may then place a screw through the drilled hole to affix the blind hole of the intramedullary nail.

Figure 16:
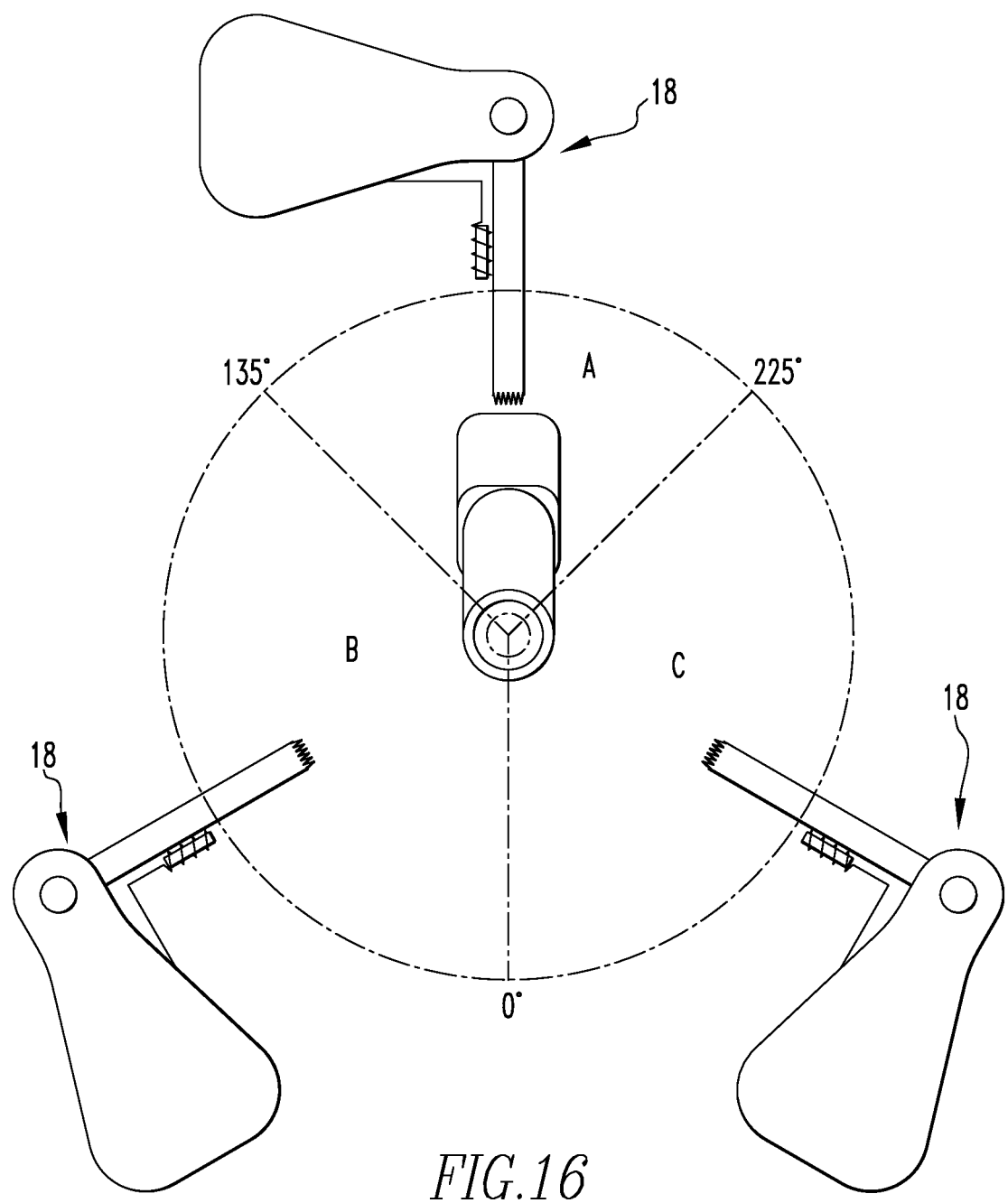
FIG. 16 is a schematic illustrating view selection criteria.

FIG. 16 illustrates a method for selecting views corresponding to landmark identifier position. In some embodiments, the view displayed on the monitor is dependent upon the location of the landmark identifier relative to the implant. The diameter of the implant is broken into sectors or fields. In the embodiment depicted in FIG. 16, the diameter is broken down into three fields: (A) 135 degrees to 225 degrees; (B) 0 degrees to 135 degrees; and (C) 225 degrees to 360 degrees. The initial view is based upon landmark identifier orientation relative to the implant. As the user moves landmark identifier toward or away from the implant, the monitor display zooms in or out on the selected field.

Figure 17:
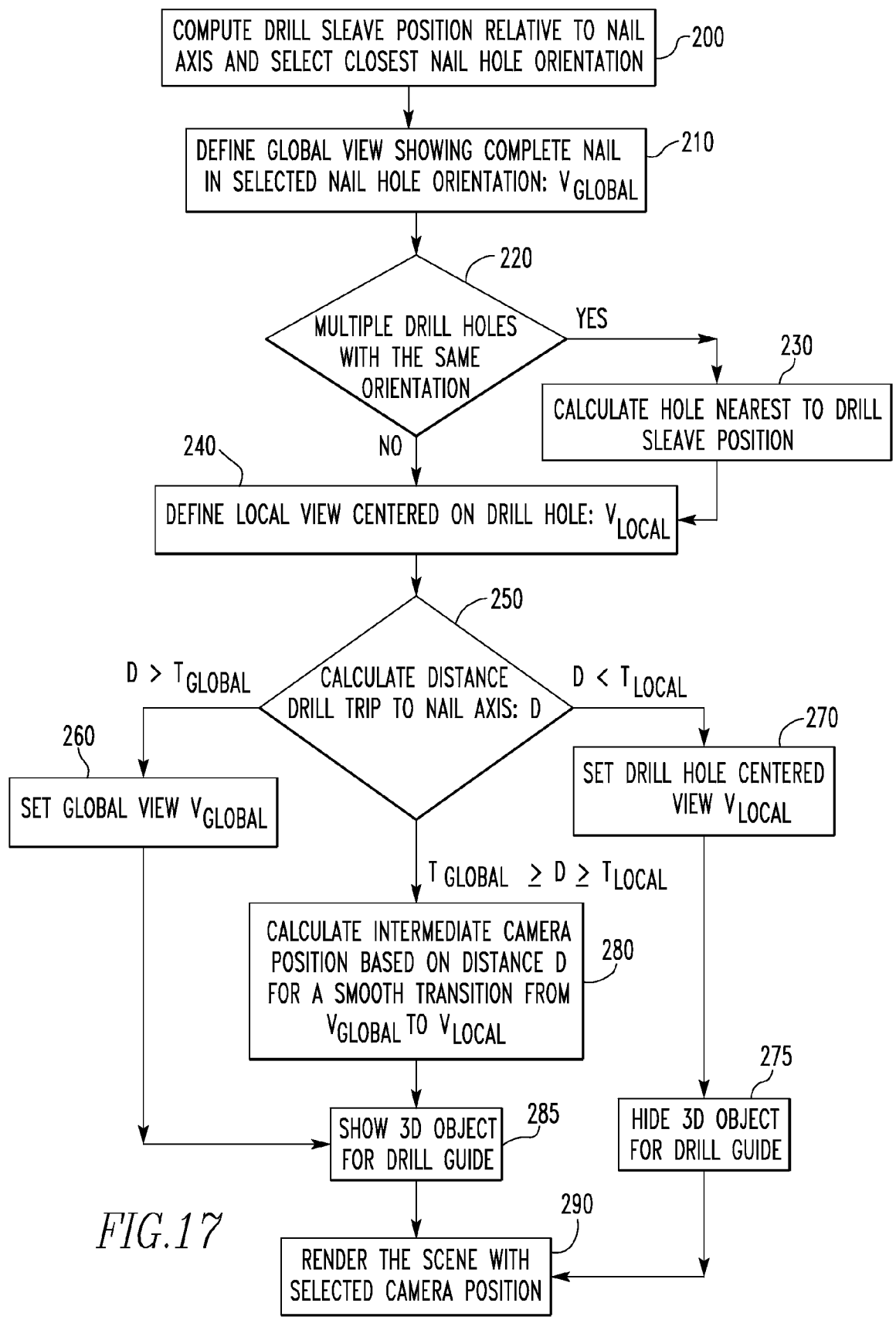
FIG. 17 is a flowchart illustrating the step of view selection.

FIG. 17 is a flowchart for view selection and display of one landmark. The process may be repeated for multiple landmarks. The processor 12 uses the transformation matrix in the following process steps. In step 200, landmark identifier position is computed relative to the implant based upon the positions of the relevant sensors, and the landmark closest the landmark identifier is selected for display. In step 210, a global view is defined showing the whole implant with the selected landmark oriented for proper viewing. A global view is analogous to viewing the implant at a distance. In step 220, there is a decision whether there are multiple landmarks having the same orientation. If yes, then in step 230, the processor calculates which landmark is nearest to the landmark identifier position and selects it for viewing. If no, in step 240, a local view is defined and centered upon the selected landmark. A local view is analogous to viewing the implant in close proximity. In some embodiments, it may be desirable to hide the landmark identifier when the local view is defined. In steps 250, 260, and 270, the processor 12 identifies the distance from landmark identifier to the landmark and depending upon the decision made, either hides or renders the landmark identifier. In step 250, the distance from landmark identifier to the landmark and a comparison is made between the calculated distance D and set variables $T_{Global}$ and $T_{Local}$. If $D > T_{Global}$, then the global view is selected in step 260 and the processor proceeds to step 285. If $D < T_{Local}$, then the local view is selected and centered upon the landmark in step 270. Thereafter, the processor proceeds to step 275. In optional step 275, the landmark identifier is hidden. Otherwise, an intermediate camera position is calculated based upon the distance D to enable a smooth transition from global view to a local view in step 280. In step 285, the landmark identifier is shown. In step 290, the scene with selected camera position is rendered.

Figure 18:
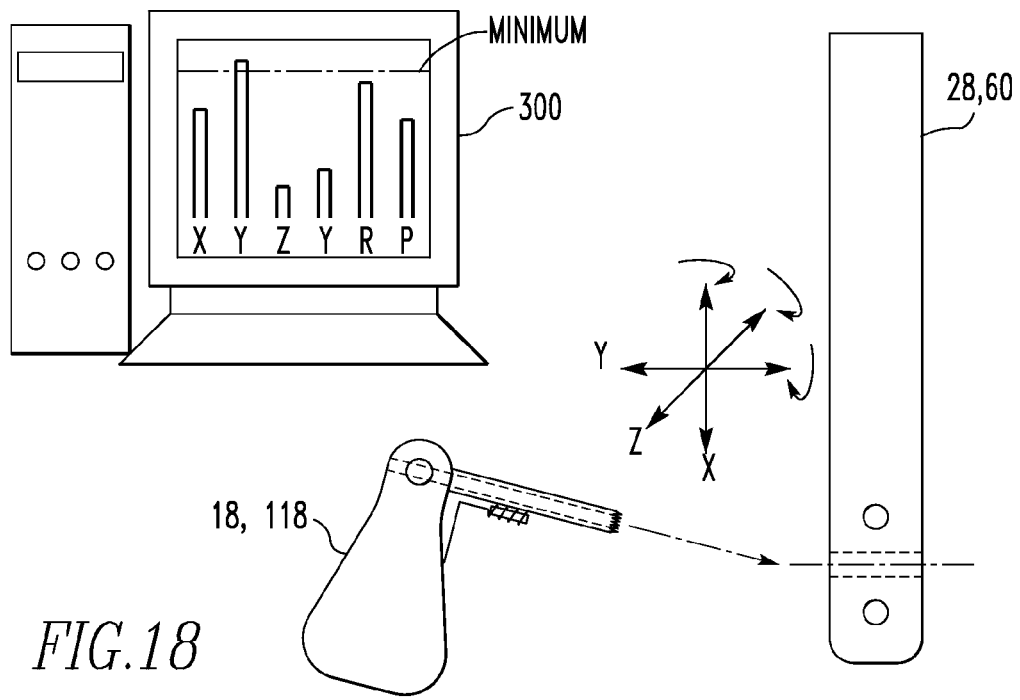
FIG. 18 is a schematic illustrating a first alternative method of aligning the landmark identifier.

FIG. 18 is a schematic illustrating a first alternative method of aligning the landmark identifier. A computer program running on the processor may be used to take the information of the at least two sensors and graphically display them in relative position (the second sensor relative to the first sensor) on the monitor. This allows the user to utilize the system to guide the placement of the landmark identifier. In the case of drilling a blind intramedullary nail hole, the system guides the user in placement of the drill sleeve and subsequently drilling accurately thru the hole in the intramedullary nail. The graphical user interface may include an alignment guide for each of the degrees of freedom. A minimum alignment level may be set such that the surgeon continues to orient the landmark identifier until each of the degrees of freedom meets the minimum alignment level for an effective placement of the landmark identifier. The example of FIG. 18 shows an instance where the placement in the Y-direction meets the minimum required tracking placement. However, none of the other translational or rotational degrees of freedom meet the minimum requirements. While the magnitudes of tracking are shown as bar graphs, other graphical representations, such as color coding, may be used.

Figure 19:
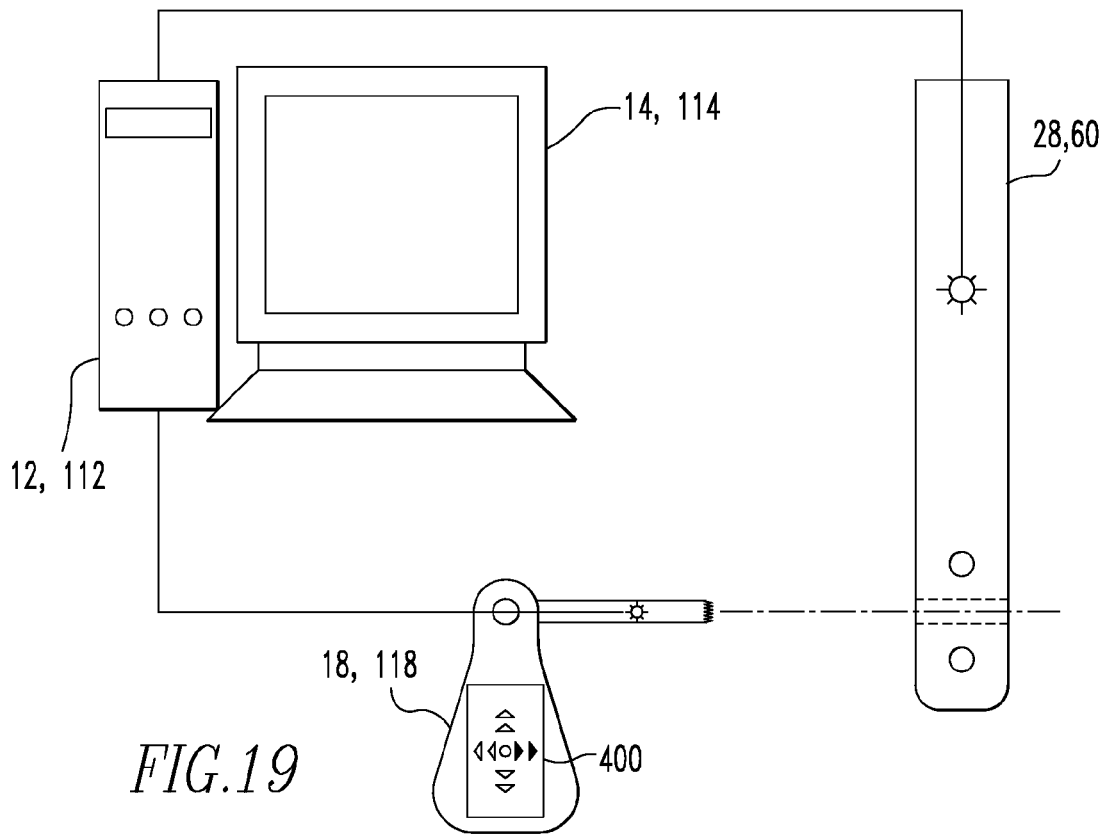
FIG. 19 is a schematic illustrating a second alternative method of aligning the landmark identifier.

FIG. 19 is a schematic illustrating a second alternative method of aligning the landmark identifier. In this embodiment, a graphical interface using a plurality of LEDs to position the drill may be placed upon the landmark identifier, such as a drill sleeve. By using the LEDs to trajectory track the drill, the surgeon may align the drill with the blind fixation hole. The trajectory may additionally use secondary displays to add more information to the system. For example, for affecting the magnitude of adjustment, the trajectory may include flashing LEDs so that high frequency flashing requires larger adjustments while low frequency flashing may require smaller adjustments. Similarly, colors may add information regarding adjustments to alignment.

Figure 20:
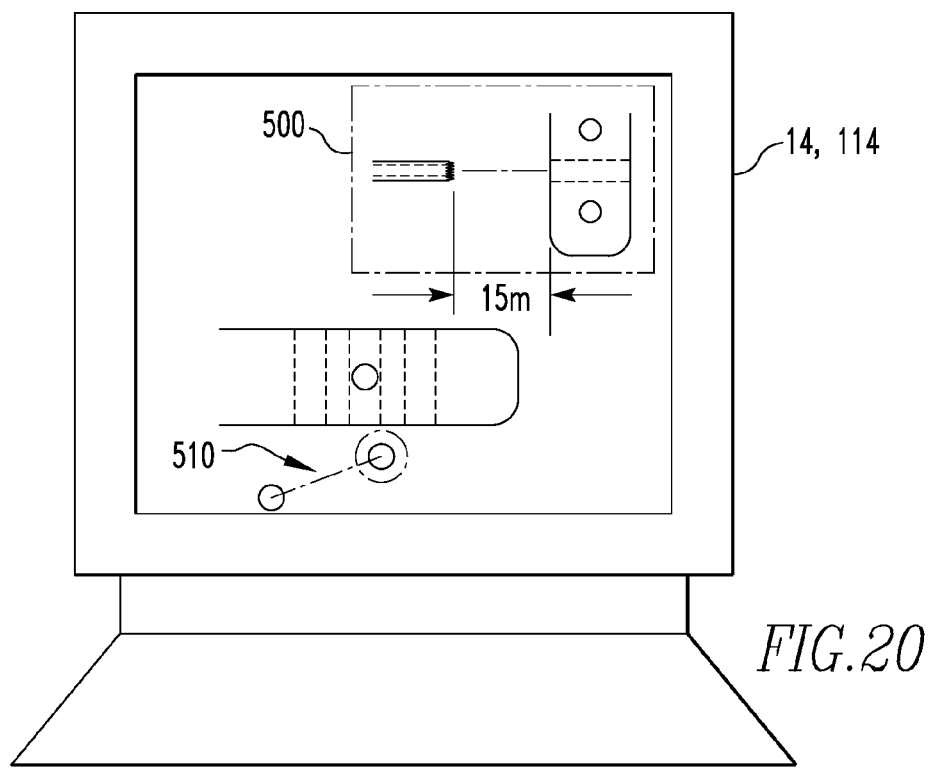
FIG. 20 illustrates a monitor with exemplary views.

FIG. 20 illustrates a monitor with exemplary views. A first portion 500 indicates the distance the drill is on each side of the implant. This may provide the user with a better understanding of drill depth and alert the user when to stop when appropriate drill depth has been achieved. The second portion 510 provides the user with alignment information. As an example, drill depth data may be obtained using the embodiment shown in FIG. 9.

Figure 21:
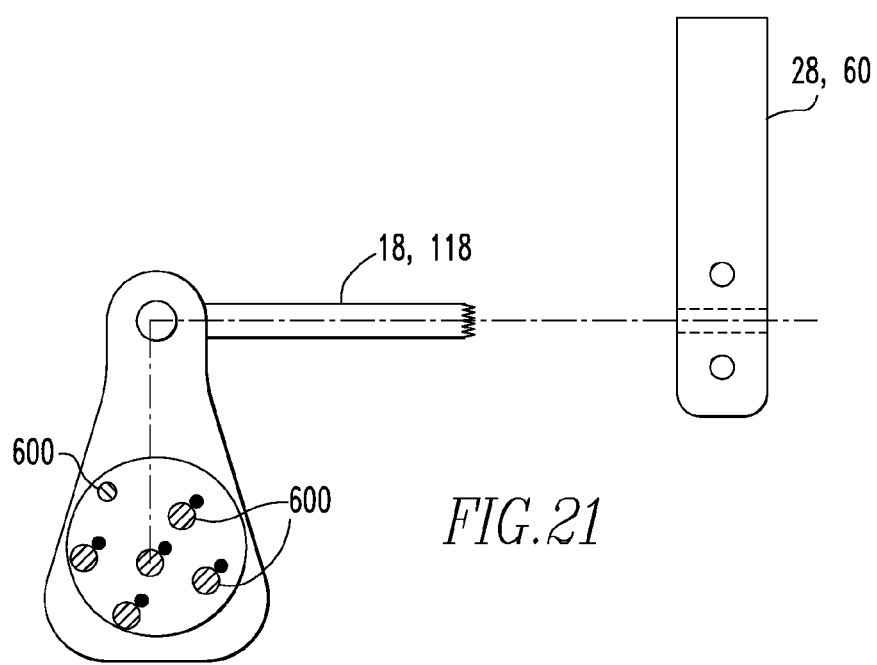
FIG. 21 illustrates an alternative embodiment of the landmark identifier.

FIG. 21 illustrates an alternative embodiment of the landmark identifier. The landmark identifier is configured to display, with LEDs, the position and trajectory information for proper alignment. The size of the LEDs may display additional information regarding the magnitude of required adjustment. The trajectory light may display a simple on/off toggle between an aligned trajectory and a mal-aligned trajectory. As another example, the trajectory LED may be color coded to suggest the magnitude of necessary adjustment for proper alignment.

Figure 22:
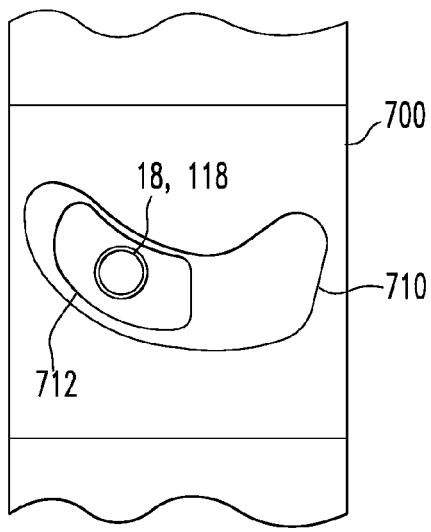
FIG. 22 illustrates a first alternative embodiment of the insertion handle.

FIG. 22 illustrates a first alternative embodiment of the insertion handle 700. The insertion handle 700 includes an arcuate slot 710. The arcuate slot limits the movement of the landmark identifier 18, 118 within the operating space. In the case of identifying a blind screw hole, the arcuate slot limits the movement of the drill sleeve for fine adjustment of its position. In some embodiments, the insertion handle 700 includes a carriage 712 that receives the landmark identifier and rides in the slot 710.

Figure 23:
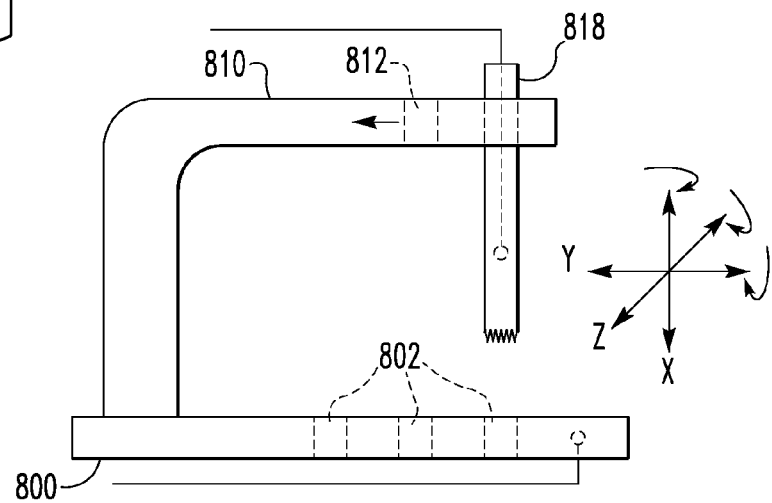
FIG. 23 illustrates the system for identifying a landmark in a third embodiment.

FIG. 23 illustrates the system for identifying a landmark in a third embodiment. In this embodiment, the orthopaedic implant 800 is a bone plate and the insertion handle 810 is a guide affixed to the bone plate. In the depicted embodiment, the inductive sensor is placed on the surface of the orthopaedic implant 800 relative to one or more landmarks. The guide 810 may allow a landmark identifier 818 to translate and/or rotate relative to the guide to properly align the landmark identifier with a landmark 802, such as a fastener hole. In addition, where multiple fixation holes are on the implant, then additional guide holes 812 on the guide 810 may help approximate the position of the additional fixation holes.

Figure 24:
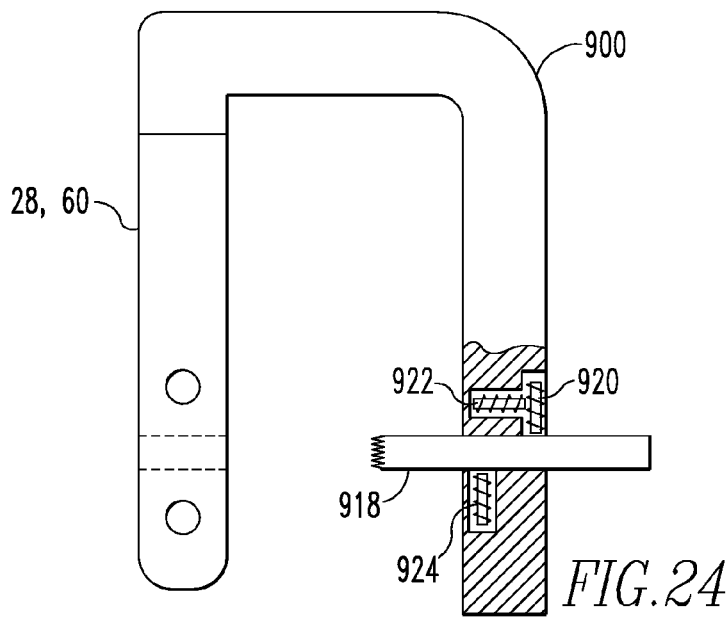
FIG. 24 illustrates a second alternative embodiment of the insertion handle.

FIG. 24 illustrates a second alternative embodiment of the insertion handle. The insertion handle 900 includes fine adjustment in landmark identifier 918 position through the use of small servomotors 920, 922, 924. The servomotors 920, 922, 924 may adjust the orientation and position of the landmark identifier 918. Control of the servos may be automatic or may be controlled by a surgeon.

In one particular embodiment, provided feedback information is selected from the group consisting of audible, visual, and tactile. The audible feedback may be output through a speaker, headphones, ear buds, or an ear piece. The audible feedback signal may be transmitted over wire or wirelessly using radio frequency or terrestrial data transmission. The visual feedback may be output through a cathode ray tube, a liquid crystal display, or a plasma display. Visual feedback devices may include, as examples, a television monitor, a personal digital assistant, or a personal media player. The visual feedback signal may be transmitted over wire or wirelessly using radio frequency or terrestrial data transmission. The tactile feedback may be output through gloves, instruments, or a floor mat. The tactile feedback signal may be transmitted over wire or wirelessly using radio frequency or terrestrial data transmission.

The invention further includes a method for identifying a landmark. The method includes the steps of: providing an orthopaedic implant assembly having an orthopaedic implant with a longitudinal groove and a removable lead having a magnetic sensor attached thereto situated within the longitudinal groove, the orthopaedic implant having a proximal end portion, a distal end portion, and at least one landmark on the distal end portion; implanting the orthopaedic implant assembly in a patient; first installing transfixion elements in the proximal end portion; identifying the at least one landmark using a landmark identifier; installing a transfixion element in the at least one landmark in the distal end portion after first installing transfixion elements in the proximal end portion; and removing the removable lead. This method allows for proximal locking of the implant prior to distal locking. This is a significant advantage over the prior art as prior devices required distal locking prior to proximal locking.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while FIG. 1 illustrates a pocket for affixing the first sensor to the implant, other structure and/or methods may be used to affix these items together. Thus, the breadth and scope of the present invention should not be limited by any of the above-described exemplary embodiments, but should be defined only in accordance with the following claims appended hereto and their equivalents.

What is claimed is:

1. A system for identifying a landmark, the system comprising:
 a. a field generator for generating a magnetic field;
 b. an orthopaedic implant configured to be placed within the magnetic field, the orthopaedic implant having at least one landmark, a proximal end, a distal end, and a longitudinal axis extending from the proximal end to the distal end, the orthopaedic implant defining:
  i. a cannulation that extends along the longitudinal axis and
  ii. a longitudinal groove that is at least partially offset from the cannulation, the longitudinal groove extending along the longitudinal axis and having a proximal end portion and a distal end portion;
  c. a first magnetic sensor configured to be placed in the distal end portion of the longitudinal groove and spaced apart from the at least one landmark a set distance;
  d. a landmark identifier that includes (i) a drill guide configured to receive a drill bit and (ii) a second magnetic sensor that is attached at a fixed position with respect to the drill guide and is configured to move with the drill guide; and
  e. configured to compare sensor data from the first and second magnetic sensors and use the set distance to calculate the position of the landmark identifier relative to the at least one landmark.

2. The system of claim 1, further comprising a third sensor for sensing a position of a removable element relative to the landmark identifier when the removable element is received in the landmark identifier.

3. The system of claim 1, wherein the cannulation and the longitudinal groove each have a central longitudinal axis, and the central longitudinal axes of the cannulation and the longitudinal groove extend generally parallel to the longitudinal axis of the orthopaedic implant.

4. The system of claim 1, wherein the cannulation extends distally from the proximal end of the orthopaedic implant, and wherein the longitudinal groove extends distally from the proximal end of the orthopaedic implant.

5. The system of claim 4, wherein the cannulation extends to the distal end of the orthopaedic implant, and wherein the longitudinal groove terminates at a location proximal of the distal end of the orthopaedic implant.

6. A system for targeting a landmark, comprising:
  a medical implant having a landmark, the medical implant defining a groove;
  a processor;
  a magnetic field sensor;
  a landmark identifier;
  a field generator for generating a magnetic field; and
  a second sensor for sensing a position of an element relative to the landmark identifier when the element is received in the landmark identifier;
  the system configured such that with the magnetic field sensor located in the groove and oriented in a predetermined position relative to the landmark, the system can be utilized to guide the placement of the landmark identifier relative to the landmark, and
  wherein the system is configured to generate data from the second sensor while the element is received in the landmark identifier, and the processor is configured to use the generated data from the second sensor to determine a depth of insertion of the element into bone.

7. The system of claim 6 wherein the field generator and the landmark identifier are spaced apart.

8. The system of claim 6 wherein the magnetic field sensor is embedded in the medical implant.

9. The system of claim 6 wherein the magnetic field sensor is wireless.

10. The system of claim 6 wherein the medical implant comprises an intramedullary nail.

11. The system of claim 6 wherein the landmark comprises a hole.

12. The system of claim 11 wherein the system is configured to be calibrated to account for an offset distance between a center of the landmark and the magnetic field sensor.

13. The system of claim 6 further comprising a lead connected to the magnetic field sensor, the lead being located in the groove.

14. The system of claim 6 wherein the magnetic field sensor is attached to a lead, and the lead and the magnetic field sensor are configured for removable receipt within the groove.

15. The system of claim 6 wherein the groove is a longitudinal groove that extends along an outer surface of the medical implant.

16. The system of claim 6 wherein the magnetic field sensor is at a known location and orientation.

17. The system of claim 6 wherein the magnetic field sensor comprises two transverse coils.

18. The system of claim 6 further comprising a guide attached to the medical implant configured to be used for installation of the medical implant and routing of a sensor lead.

19. The system of claim 6 further comprising a display for use in guiding the placement of the landmark identifier relative to the landmark.

20. The system of claim 19 wherein the system is configured to switch between providing gross tracking information and fine tracking information on the display.

21. The system of claim 6 wherein the medical implant defines a longitudinal cannulation, and wherein the groove comprises a longitudinal groove with a proximal end and a distal end, the longitudinal groove being at least partially offset from the longitudinal cannulation.

22. The system of claim 6, further comprising a cover at an exterior of the medical implant,
  wherein the medical implant has a proximal end and a distal end,
  wherein a portion of the groove is disposed between the proximal end and the distal end, and
  wherein the cover is disposed over at least the portion of the groove.

23. The system of claim 22, wherein the medical implant has a shaft and the shaft has an external surface between the proximal end and the distal end, the shaft defining an opening to the groove through the external surface, and the external surface defining a recess around the opening, and
  wherein the cover is located over the opening and in the recess such that an outer surface of the cover is substantially flush with the external surface of the shaft.

24. The system of claim 22, wherein the cover is formed of a metal foil.

25. The system of claim 6, wherein the second sensor is located to sense one or more indicators on the element as the element moves relative to the landmark identifier.

26. The system of claim 22, wherein the element is a drill bit, and the indicators are markings on the drill bit.

27. The system of claim 22, wherein the second sensor is configured to generate data indicative of a distance that the element is translated relative to the landmark identifier along an axis defined by the landmark identifier.

28. The system of claim 6, wherein the second sensor is configured to interact with the element and generate data based on the interaction with the element; and
  wherein the second sensor is attached to and configured to move with the landmark identifier.

29. A system for targeting a landmark, comprising:
  a medical implant having a landmark;
  a magnetic field sensor;

a landmark identifier;

a field generator for generating a magnetic field; and one or more processing devices configured to determine a distance of the landmark identifier relative to the medical implant and output data for visual representations of the medical implant;

the system configured such that with the magnetic field sensor oriented in a predetermined position relative to the landmark, the system can be utilized to guide locating of the landmark identifier relative to the landmark;

the one or more processing devices being configured to switch, based on a distance of the landmark identifier to the medical implant, between (i) providing data for a zoomed-in view of the medical implant and (ii) providing data for a zoomed-out view of the medical implant.

30. The system of claim 29 wherein the one or more processing devices are configure to provide, for display, first data that indicates the distance of the landmark identifier to the medical implant and second data that indicates alignment information for an alignment of the landmark identifier relative to the landmark.

31. The system of claim 29, wherein the one or more processing devices are configured to:

select a view from among multiple different views of the medical implant based on the location of the landmark identifier relative to the medical implant; and provide, for display, information indicating the selected view of the medical implant.

32. The system of claim 31, wherein the one or more processing devices are configured to select the view from among multiple different views that each correspond to different angular range with respect to the medical implant.

33. A system for targeting a landmark, comprising:

a medical implant having a landmark, the medical implant defining a groove;

a magnetic field sensor;

a landmark identifier;

a field generator for generating a magnetic field; and a second sensor for sensing a position of an element relative to the landmark identifier when the element is received in the landmark identifier;

the system configured such that with the magnetic field sensor located in the groove and oriented in a predetermined position relative to the landmark, the system can be utilized to guide the placement of the landmark identifier relative to the landmark, and the system configured such that with the element received in the landmark identifier, data from the second sensor can be utilized to determine a depth of insertion of the element into bone, wherein the second sensor is located to sense one or more indicators associated with the element as the element moves relative to the landmark identifier, and wherein the element is a drill bit, and the indicators are markings on the drill bit.

* * * * *

UNITED STATES PATENT AND TRADEMARK OFFICE
CERTIFICATE OF CORRECTION

PATENT NO. : 8,739,801 B2  Page 1 of 1
APPLICATION NO. : 12/527997
DATED : June 3, 2014
INVENTOR(S) : Rains et al.

It is certified that error appears in the above-identified patent and that said Letters Patent is hereby corrected as shown below:

On the Title page, at Item [75] Inventors, replace "Solothum" with --Solothurn--.

On Title page 3, Item [56] "Other Publications", Col. 2, line 9, replace "Eurpoean" with --European--.

On Title page 3, Item [56] "Other Publications", Col. 2, line 22, replace "wth" with --with--.

On Title page 3, Item [56] "Other Publications", Col. 2, line 23, replace "on on" with --on--.

On Title page 3, Item [56] "Other Publications", Col. 2, line 26, replace "Heathcare" with --Healthcare--.

On Title page 3, Item [56] "Other Publications", Col. 2, line 36, replace "Soluations" with --Solutions--.

In the Drawings
Fig. 17, element 200, replace "SLEAVE" with --SLEEVE--.
Fig. 17, element 230, replace "SLEAVE" with --SLEEVE--.

In the Specification
Col. 7, line 49, replace "cross-layer" with --cross-layered--.

In the Claims
Claim 1, at Col. 13, line 17, replace "e." with --e. a processor--.
Claim 26, at Col. 14, line 54, replace "claim 22" with --claim 25--.
Claim 27, at Col. 14, line 56, replace "claim 22" with --claim 25--.

Signed and Sealed this
Sixteenth Day of December, 2014

Michelle K. Lee
*Deputy Director of the United States Patent and Trademark Office*